United States Patent
Leszcyniecka et al.

(10) Patent No.: US 9,868,973 B2
(45) Date of Patent: Jan. 16, 2018

(54) METHOD FOR OPTIMIZING POST-TRANSLATIONAL MODIFICATIONS ON RECOMBINANT PROTEINS

(71) Applicant: STC Biologics, Inc., Cambridge, MA (US)

(72) Inventors: Magdalena Leszcyniecka, Cambridge, MA (US); Sergey Shulga-Morskoy, Cambridge, MA (US)

(73) Assignee: STC Biologics, Inc., Cambridge, MA (US)

(*) Notice: Subject to any disclaimer, the term of this patent is extended or adjusted under 35 U.S.C. 154(b) by 0 days.

(21) Appl. No.: 15/111,260

(22) PCT Filed: Jan. 13, 2015

(86) PCT No.: PCT/US2015/011226
§ 371 (c)(1),
(2) Date: Jul. 13, 2016

(87) PCT Pub. No.: WO2015/106276
PCT Pub. Date: Jul. 16, 2015

(65) Prior Publication Data
US 2016/0340706 A1  Nov. 24, 2016

Related U.S. Application Data (60) Provisional application No. 61/926,603, filed on Jan. 13, 2014.

(51) Int. Cl.
*G01N 33/68* (2006.01)
*C12P 21/02* (2006.01)
*C07K 16/32* (2006.01)

(52) U.S. Cl.
CPC ............ *C12P 21/02* (2013.01); *C07K 16/32* (2013.01); *C07K 2317/14* (2013.01); *C07K 2317/24* (2013.01); *C07K 2317/41* (2013.01); *C12N 2510/02* (2013.01); *G01N 2440/00* (2013.01)

(58) Field of Classification Search
CPC .......... G01N 2440/00; G01N 2440/38; G01N 33/68; C07K 2317/14; C07K 2317/41
See application file for complete search history.

(56) References Cited

U.S. PATENT DOCUMENTS 6,780,607 B2 *  8/2004  Choi ................... C07K 14/505
                                                              435/175
2015/0344587 A1 * 12/2015  Wong .................. A61K 31/517
                                                              424/133.1

FOREIGN PATENT DOCUMENTS

WO         WO-13067322 A1 *  5/2013

OTHER PUBLICATIONS

Walsh 2010; Post-translational modifications of protein biopharmaceuticals. Drug Discovery Today 15(17/18): 773-780.*
Berkowitz et al. 2013; Analytical tools for characterizing biopharmaceuticals and the implications for biosimilars. Nat Rev Drug Discov 11(7): 527-540.*

* cited by examiner

*Primary Examiner* — Karen Cochrane Carlson
(74) *Attorney, Agent, or Firm* — Hahn Loeser & Parks, LLP; Robert M. Gould (57) ABSTRACT

A method for optimizing post-translational modifications of recombinant proteins expressed in living cells is described. More particularly, a method for modulation of host proteins in living cells that control PTMs on recombinant proteins is described that has particularly useful applications in developing manufacturing process changes or in biosimilar development. The goal of this modulation is to produce a recipe for production of a recombinant protein in the new process or in the biosimilar that will produce a targeted PTM profile in the resulting protein product. In the method one or more modulators are selected, as from a modulator library, which affect the activity of host proteins. These modulators are added to media during production such that the resulting product matches the PTMs of the reference product. The ideal set of modulators and their concentrations are identified through a unique iterative process and the combined modulators and their concentrations constitute a recipe for growth media for the production of said recombinant protein. The methodology to obtain such a recipe described herein may then be used in many applications, such as optimizing new batches of recombinant protein drugs, developing biosimilar or bio-better drugs.

17 Claims, 3 Drawing Sheets

Figure 1 Examples of inhibitors in glycosylation pathway

| Enzyme Name | Reaction | Inhibitors |
|---|---|---|
| N-acetyl glucosaminyl transferase (GnT I) | Man5 –> Man5-GlcAc | Tunicamycin, (1) UDP-GlcAc derivatives |
| Fucosyltrasferase | G0 –> G0F | 2F-Peracetyl-Fucose, GDP-Fucose derivatives (2) |
| Galactosyltransferase | G0F –> G1F –>G2F | Plenty of academic publications about synthesis of novel inhibitors. Very specific could identified with screening. (3) |
| α-2,3-sialyltransferase | G2F –>G2FS | Lithocholic acid analogues, peptides (4) |
| Mannosidase | Man9 -> Man5 | Kifunensine, Swainsonine (5) |

Figure 2 Schematic view of the glycosylation pathway in a CHO cell line

Figure 3 Example of a chromatogram showing the carbohydrate peaks using the 2AB method of carbohydrate analysis.

METHOD FOR OPTIMIZING POST-TRANSLATIONAL MODIFICATIONS ON RECOMBINANT PROTEINS

FIELD OF THE INVENTION

The present invention relates to the controlled manufacture of recombinant proteins having post-translational modifications (PTMs) from living cells. More particularly, the present invention relates to the modulation of host protein activity in living cells to control the PTMs of the recombinant proteins they produce. The method is particularly useful in the development of manufacturing processes and when making changes to manufacturing methods for biosimilar products. The goal of this method is to produce a recipe for the production of a recombinant protein or a biosimilar product using a process that may be different from the original but that yields a recombinant protein with a targeted set of PTMs or, depending on the circumstances, with a very similar or identical PTM profile when compared to a reference product.

BACKGROUND OF THE INVENTION

Figure 1:
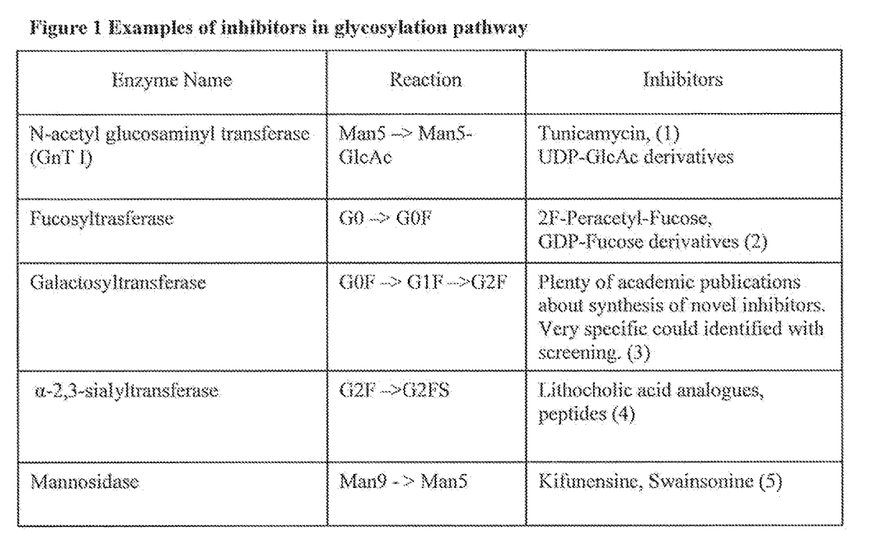
FIG. 1 contains the list of examples of host proteins and some of the known inhibitors.

Recombinant proteins are produced in living cells and are a major class of biologic drugs used to treat a wide range of diseases. Production of recombinant proteins in cell culture is complicated by the fact that a cell's host proteins can modify recombinant proteins by adding a variety of PTMs, such as glycosylation, carboxylation, hydroxylation, sulfation and amidation, deamidation, among others. Some examples of inhibitors are shown in FIG. 1. Some host proteins, including but not limited to Carboxypeptidase B, can even modify recombinant proteins by removing amino acids from the sequence, such as C-terminal lysines. PTMs are very difficult to control during production of recombinant proteins, especially if a specific PTM is required; such as during biosimilar production or when making manufacturing process changes.

The goal of biosimilar development is to produce a biosimilar product with a similar and ideally identical PTM profile to a reference product or protein of interest. The capability of producing a recombinant protein copy that displays minimal or no differences from a marketed reference product can simplify the clinical testing required for drug approval and should reduce the cost of biosimilar drug development. One major reason for the more limited requirement for clinical studies with biosimilars is that the safety risks are known when product attributes are the same between a biosimilar and its reference product. Large hurdles in biosimilar development are related to the fact the production process for many commercial biologic drugs is either not known, may be protected by patents, or is outdated (i.e. use of animal derived products).

Thus, it is necessary to develop a production process that may be different from the original process but that still yields a copy of the reference product (biosimilar) with the same, or similar PTMs as the reference product.

Similarly, during a manufacturing process change, the ability to match PTMs on a recombinant protein before and after process changes is of uttermost importance. The key reason for a process change for a recombinant protein is to improve the cell line performance, to increase productivity, and to increase cell stability without changing PTMs of said recombinant protein. A method is needed that can decouple the optimization of productivity of the cell line from optimization of PTMs.

In order to develop such a method the host proteins that need to be modulated must be identified and modulators necessary to modulate those host proteins are then selected. Host proteins include enzymes involved in glycosylation, carboxylation, hydroxylation, deamidation, oxidation, C-terminal sulfation, C-terminal carboxylase and amidation or any other posttranslational modification. Modifying the activity of these enzymes using small molecules, natural products, biologics, RNAi, RNA, or DNA can be used for production of a recombinant protein with target PTMs. A method that is capable of modifying PTMs on biologic molecules would be far superior for use in the production of biosimilar and biobetter biologics than known systems that knock-out PTMs altogether. Such systems could be used to produce biologic molecules having PTMs within target ranges as opposed to knock out technologies which have no possibility of targeting a desired PTM range.

SUMMARY OF THE INVENTION

The present invention provides methods for optimization of cell culture processes to yield recombinant proteins with target PTMs that are uniquely useful for biosimilar development and manufacturing process changes. The method focuses on optimization of cell culture conditions via addition of modulator(s) to growth media containing living cells that produce proteins, such as recombinant proteins or biosimilar proteins. Addition of modulator(s) to the living cell culture medium can be used to reduce or augment the activity of specific host protein(s) that control PTMs on the biosimilar drug target.

The methods described herein are useful for optimization of cell culture conditions to produce recombinant proteins with a target PTM profile which can be identified on a reference product. The methods described herein are particularly useful during process changes and in biosimilar development.

The method involves developing a recipe, to produce a recombinant protein with target PTMs.

In one aspect of the invention, there is provided a method for optimization of PTMs on a recombinant protein during process change via modulation of host protein activity:
  a) Measuring different PTMs on reference standards or other drug batches produced using a defined process. Three to five batches are usually recommended by the regulatory agencies however any number of batches can be examined.
  b) Setting target ranges for the PTMs on the recombinant protein based on data generated in a).
  c) Selecting a plurality of growth media and one or more modulators. Modulators can be selected from a library of modulators.
  d) Growing living cells expressing the recombinant protein in the presence of the selected modulator(s).
  e) Isolating the product from d) and comparing its PTMs to the target set in b).
  f) Repeating steps c), d), and e) with additional modulators and or at different modulator concentrations to match PTMs set in b). The modulators can be used alone or in a combination with each other. The set of exact modulation required to obtain the target PTMs provides a recipe for the production of said recombinant protein. The PTMs should not be outside the specifications set for said reference standard.

In another aspect of the invention, there is provided a method for optimizing PTMs on a biosimilar via addition of a selected set of modulators to influence the activity of host cell proteins. The method involves:

a) Measuring PTMs on a commercial reference product(s). At least three batches of reference product should be analyzed however studying more batches may help to increase the range in target PTMs.

b) Setting target ranges for the PTMs for a biosimilar product for that commercial reference product.

c) Selecting a plurality of growth media and one or more modulators which can be selected from a modulator library.

d) Growing the living cells expressing the biosimilar product in the presence of the modulator(s).

e) Isolating the biosimilar product from d) and comparing its PTMs to the target range set in b).

f) Repeating steps c), d), and e) with additional modulators and or at different modulator concentrations to match PTMs set in b). The modulators can be used alone or in a combination with each other. The set of exact modulation required to obtain the target PTMs provides a recipe for the production of said recombinant protein. The PTMs should not be outside the specifications set for said biosimilar product.

The modulators are selected to modulate the activity of host proteins responsible for producing PTMs. The PTMs may include, but are not limited to, any of the following post-translational modifications: glycosylation, carboxylation, deamidation, oxidation, hydroxylation, O-sulfation, amidation, glycylation, glycation, alkylation, acylation, acetylation, phosphorylation, biotinylation, formylation, lipidation, iodination, prenylation, oxidation, palmitoylation, phosphatidylinositolation, phosphopantetheinylation, sialylation, and selenoylation, C-terminal Lysine removal.

The outcome of the process optimization for a recombinant protein is a recipe for media that includes concentrations of a variety of modulators that are required to produce a recombinant protein or a biosimilar product with target PTMs.

The process of altering the cell culture conditions and determining additional recipes may be repeated until the target PTMs are obtained.

The method for optimization may be used in conjunction with a bioreactor, shake flask or a wave bag or any other method known to one skilled in the art of process development. Assays selected for their ability to detect and measure the presence of specific PTMs are used to measure PTMs. The assay module may be in liquid communication with the bioreactor for delivery of a recombinant protein to the assay module or can be carried out manually. The method can be implemented using a system having a library of individual modulators, which may be in liquid communication with the cell culture media and can be controlled by the assay module for transfer of individual modulators into the bioreactor, a shake flask or other cell culture container.

The foregoing summary and detailed description is better understood when read in conjunction with the accompanying drawings, which are included by way of example and not by way of limitation.

DETAILED DESCRIPTION OF EMBODIMENTS

It is to be understood that the terminology used herein is for the purpose of describing particular embodiments only, and is not intended to be limiting. Further, unless defined otherwise, all technical and scientific terms used herein have the same meaning as commonly understood by one of ordinary skill in the art to which this invention pertains.

In describing and claiming the present invention, the following terminology and grammatical variants will be used in accordance with the definitions set forth below.

The term "living cell," as used herein, refers to cell used for production of a biosimilar version of a recombinant protein drug. Examples of a living cell include but are not limited to human, sheep, goat, cow, dog, cat, chicken, hamster, mouse, tobacco plant, and carrot sources. Examples of living cells which are commonly used to produce recombinant proteins as active drug ingredients include mammalian cells such as Chinese Hamster Ovary cells (CHO), murine myeloma NS0 cells, Baby Hamster Kidney (BHK) cells, SP2/0, 293, or CAP-T cells.

The term "host proteins" refers to proteins present in living cells, which interact with and modify recombinant proteins expressed in said living cells.

The term "modulators" include small molecules, biological compounds, natural products, lipids that can modulate the activities of host proteins that can be added to the solution containing living cells that can specifically alter post-translational modifications on recombinant proteins. Modulators include both inhibitors and activators of host cell posttranslation modification proteins. Modulator library refers to a collection of modulators that can be used to alter the activity of host proteins either to activate them or to inhibit them. The library of modulators may include small molecule drugs such as fucosyl transferase inhibitors, mannosidase inhibitor, biologic molecules such insulin, RNAi and RNA molecules, and other biomolecules known to those skilled in the art would recognize to affect post translational modifications of recombinant proteins or their biosimilars being produced in host cells.

In certain methods and embodiments one or more of the following compounds, known for purposes of this disclosure as Group I inhibitors, can be used to modulate PTMs: 4,6,6'-trichloro-4,6,6'-trideoxy-1',2-isopropylidene-3,3',4'-tri-O-acetylgalactosucrose; hexa-O-benzoyl-4,6-O-isopropylidenesucrose; methyl 4,6-dichloro-4,6-dideoxy-α-D-galactopyranoside; methyl 2,3-di-O-tosyl-4,6-O-benzylidine-α-D-glucoside; 6'-chlorosucrose; 2,3,4-trichloro-2,3,4-trideoxy-1',3',4',6'-tetraacetylgalactosucrose; 4,6-O-benzylidene-6'-acetylsucrose; myo inositol hexaacetate; 3,3',4',6'-tetra-O-acetylsucrose; 3,4,6,3',4',6'-hexa-O-acetylsucrose; 6,6'-diamino-6,6'-dideoxy-sucrose; D-glycero D-guloheptose; 2,3,1',3',4',6'-hexa-O-acetyl-4,6-O-orthobutyrylsucrose; 2,3,6,3',4'-penta-O-acetyl-1',6'-di-O-tritylsucrose; 3,6,3',6'-dianhydrotrehalose; 2,3,6,3',4'-penta-O-acetyl-4 chloro-4-deoxy sucrose; 1,6-anhydro-3-nitro-3-deoxy-b-D-gulose; methyl 4,6-O-benzylidene sophroside; sucrose 4,6,1',6'-tetratrityl 2,3,3',4'-tetraacetate; 4,4',6'-trichloro-4,4',6'-trideoxygalactosucrose; 4,6,1',6'-tetrachloro-4,6,1',6'-tetradeoxysucrose; trichlorogalactosucrose 6 teriary butyl diphenyl sialyl; 2,3:4,5-di-O-isopropylidine-β-D-fructopyranose; trichlorogalactosucrose 3',4'lyxoepoxide triacetate; 6'chloro-6'-deoxy-2,3,4,6,1',3',4'-hexa-O-acetylsucrose; 4,6,1',6'-tetra-O-trytyl-2,3,3',4'-O-acetylsucrose; 6,6'-dichloro-6-6'-dideoxysucrose; 3,4,6-trichloroglucose; isomaltulose octaacetate; 6-benozyl-1',6'-ditosyl-2,3,4,3',4'-penta-O-acetylsucrose; 2,3dimethyl trichlorogalactosucrose triacetate; 1',6'-dichloro-1',6'-dideoxy-2,3,4,6,3',4'-hexa-O-acetylsucrose; 6,6'-di-O-trytyl-2,3,4,1',3',4'-hexaacetyl sucrose; octaacetyl α D-cellobiose; 6-chloro-6-deoxygalactose; 4,1',4',6'-tetrachloro-4,1',4',6'-tetradeoxy-2,3,6,3'-tetra-O-acetylgalactosucrose; 6-O-acetyl-1,2,-O-isopropylidine-α-D-glucofuranose; 2,3,4,6-tetra-O-trytyl glucose; 2,3:4,5-di-O-isopropylidinefructopyranosyl chloride; 4,6,6'-trichloro-4,6,6'-deoxy-3',4'-anhydrosucrose; 6-chloro-6-deoxy-2,3,4,1',3',4',6'-hepta-O-acetylsucrose; N-octyl D-glucamine; 2,3,4,6-tetra-O-trytyl glucose; 1',2:4,6-di-O-isopropylidine-3,3',6'-tri-O-acetyl sucrose; 2,3:4,6-di-O-isopropylidine-3',4',6'-tri-O-benzoyl-1'-acetylsucrose; 1',2:4,6-di-O-isopropylidine-3,4'-di-O-acetyl-3',6'-di-O-benzoylsucrose; 1',2:4,6-di-O-isopropylidine-3,3',4',6'-tetra-O-acetylsucrose; 6-deoxy-6-carboxymethyl-1,2,3,4-tetra-O-trytyl glucospyranoside; 2,3,4,3',4',6'-hexa-O-acetylsucrose; 1',6'-dichloro-1',6'-deoxy-2,3,4,6,3',4',6'-hexa-O-sucrose hexaacetate; 1',2,4,6-di-O-isopropylidine sucrose; 3,4-anhydro-1,6-dichloro-1,6dideoxy-β-D-lyxo-hexofuranosyl-3, 6-anhydro-4-chloro-4-deoxy-α-D-galactopyranoside; 3,3', 4',6'-benzoyl sucrose; tetraacetyl glucuronic acid; 1,2,3,4,5-penta-O-acetylxylitol; benzyl β-D-fructopyranoside; 3,3',4', 6'-tetra-O-cyclohexanoyl sucrose; phenyl β-D-galactoside; 2,3,4,6,1,2,3,6-octa-O-acetylmaltose; 2,3,4,6,1',3',4'-hepa-O-acetyl sucrose; 1',2:4,6-di-O-isopropylidine-3,6'diacetyl sucrose; β-D allose; 6'-chloro-6'-deoxy sucrose; 6-O-methyl-4,1',6'-trichloro4,1',6'-trideoxygalactosucrose; 1',4-di-O-mesyl-6'-O-benzoyl-2,3,6,3',4'-penta-O-acetylsucrose; 6'-O-benzoyl-2,3,6,3',4'-penta-O-acetylsucrose; 2,3,4,6,1', 3',4',6'-hexa-O-mesylsucrose; Methyl 4,6 O-benzylildene sophorose; Methyl 6-O-trytyl-2,3,4-tri-O-benzoyl-α-D-glucopyranoside; 6't-butyldiphenylsilyl sucrose; 1,2:3,5-di-O-phenyl-6-deoxy-6-thioacetyl-α-D-glucofuranose; 1,3,4-tri-O-acetyl-6-chloro-2,6-dideoxy-α-D-glucopyranoside; 6-O-trytyl-1,2,3,4-tetra-O-acetyl-α-D-glucopyranoside; 4,6-O-isopropylidine-2,3,1',3',4',6'-hexa-O-benzoyl sucrose; methyl 2,3-di-O-benzoyl-4,6-di-O-mesylglucopyranoside; 4,1',6'-trichloro-4,1',6'-trideoxy-2,3,6,3,4-penta-O-acetyl sucrose; methyl 4,6-O-benzylidine-2,3-di-O-tosyl-α-D-allopyranoside; 2,3,4,6-tetra-O-trytyl glucpyranose; methyl 4,6-O-benzylidine-2,3-di-O-tosyl-α-D-glucopyranoside; Di-O-trytyl-2,3,4,6,3',4'-hexa-O-acetyl sucrose; 4,6:1',2-di-O-isopropylidine-3,3',4',6'-tetra-O-acetyl sucrose; 1',2:4,6-di-O-isopropylidine sucrose; 6,3',4'-tri-O-acetyl-4,1',6'-trichloro-4,1',6'-trideoxy galactosucrose; 6'-chloro-6'-deoxy sucrose; 7-O-trytyl 2,3,4,5,6-penta-O-acetyl-D-glycero-D-gulo-heptose diethyl dithio acetal; 6'-chloro-2,3,4,6,1',3',4'-hepta-O-acetyl sucrose; 3-acetamido-1,6-anhydro-2,4-di-O-acetyl-3-deoxy β-D-gulose; Methyl 3-benzymido-4,6-O-benzylidine-3-deoxy-α-D-altropyranose; 4,1',6'-trichloro-4, 1',6'-trideoxy galactosucrose (sucralose); Methyl 3-acetamido-2,4-di-O-acetyl-3,6-dideoxy-α-L-hexoside; methyl 2,3-di-O-benzyl-4,6-di-O-mesylglucopyranoside; D-ribo-3,4,5,6-tetra-O-acetyl-1-nitro-hex-1-ene; 2-O-methyl-D-glucose diethyl dithio acetal; Methyl 3-acetamido-2,4,6-tri-O-mesyl-α-D-mannoside; D arabo-3,4,5,6 tetra-O-acetyl-1-nitro-hex-1-ene; 1,1-diethyl sulphonyl-(2-O-tosyl-α-D-arabinopyranosyl) methane hydrate; Methyl glucoside laurate; Methyl 2,3-anhydro-4,6-O-benzylidine-β-D-talopyranoside; Methyl 2,3-anhydro-4,6-O-benzylidine-β-D-talopyranoside; 3-acetamido-2,4-di-O-acetyl-1,6-anhydro-3-deoxy-β-D-idopyranose; 1,1-diethylsulphonyl-(3,4-O-isopropylidene-2-O-tosyl-α-D-arabinopyranosyl) methane hydrate; 2,3,4,5-tetra-O-benzoyl galactose; D-manno-3,7-anhydro-4-methoxy-5,6-isopropylidine-2,2-diethyl sulphonyl heptane; 2-acetamido-1,2-dideoxy-1-nitro-D-manitol; 1,1-diethylsulphonyl-L-arabo-2,3,4,5-tetra-hydroxyhexane; 1',6'-dichloro-1',6'-deoxysucrose; Methyl 3-acetamido-3-deoxy-2,4,6-tri-O-acetyl α-D-mannopyranoside; Methyl 3-benzamido-4,6,-O-benzylidine-3-deoxy-2-O-mesyl-α-D-altropyranoside; Methyl 2-O-tosyl-4,6-O-benzylidene-α-D-glucopyranoside; 3 amino-1,6-anhydro-3-deoxy-β-D-altropyranose hydrochloride; Methyl 3-N-acetyl 3,6-dideoxy-2,4 di-O-acetyl-α-L-mannoside; Methyl 4,6-diazido-α-D-galactopyranoside; 6,4',1'',6''-tetrachloro-6,4', 1'',6''-tetradeoxy raffinose; 6,6'-dichloro-6,6'-dideoxy-3,4,3', 4'-tetra-O-acetyl-sucrose; 1,1-diethylsulphanyl 1-(α-D-lyxopyranosyl)-methane; D-xylo-3,4,5,6-tetra-O-acetyl-1-nitro-hex-1-ene; 1,1-diethylsulphanyl-1-(2,3,4 tri-O-acetyl-α-D-lyxopyranosyl)-ethane; 2,3,4,6-tetra-O-acetyl galactopyranose; 1-deoxy-1-nitro-D-glycerol-D-galactoheptitol; Methyl 4,6-diazido-2-O-benzoyl-3-O-mesyl α-D-glucopyranoside; 2-O-isopropylidien-3-acetamido-3-deoxy-α-D-allofuranose; 3,6-dideoxy-3-dimethylamine-L-mannose hydrochloride; 3-acetimido-1,2,4-tri-O-acetyl-3,6-dideoxy-β-L-glucopyranose; 2 (NHPO(OPh)2)-3,4,6 triacetyl glucosazide; 2,3,6,3'-tetraacetyl 4,1',4',6'tetrachloro 4,1',4',6'tetradeoxy galactosucrose; Arabinose diethyl mercaptal; 2-chloro-3-benzamino methyl hexaside; 1'-O-trytyl-2,3,4,6,3',4',6'-hepta-O-acetylsucrose; 2,1'-O-diphenyl silane3,4,6,3',4',6'-hexa-O-acetyl sucrose; 2,3,4-trichloro-2, 3,4-trideoxy fructose; D-glycero-D-guloheptose diethyl dithio acetal; 1L-2-O-methyl-1-chiro-inositol pentabenzoate; Stevia glycoside; 4,1',6'-trichlorotrideoxygalactosucrose tetraacetate OH-6; sucrose ethyl 4,6-orthoacetate hexaacetate; sucrose methyl 4,6-orthobutyrate hexaacetate; sucrose methyl 4,6-orthoacetate hexaacetate; 4,1',6'-tribromotrideoxygalactosucrose pentaacetate; 6-O-benzoyl-4,1', 6'-trichlorotrideoxygalactosucrose tetraacetate; methyl 6-chloro-6-deoxy-α-D-galactopyranoside; methyl 4,6-dichloro-4,6-dideoxy-α-D-galactopyranoside; methyl 4,6-dichloro-4,6-dideoxy-α-D-glucopyranoside; 3,6:1',4':3',6'-trianhydro-4-chloro-4-deoxygalactosucrose; 3',6'-anhydro-4, 6,1'-trichloro-4,6,1'-trideoxygalactosucrose; 4,1',6'-trichlorogalactosucrose-3',4'-lyxoepoxide triacetate; 4,6'-dichloro-4,6'-dideoxygalactosucrose hexaacetate; 4,1',4',6'-tetrachlorotetradeoxygalactosucrose tetraacetate; 6,1',6'-trichlorotrideoxysucrose pentaacetate; 1',6'-dichloro-1',6'-dideoxysucrose pentaacetate OH-4; 4,6,1',4',6'-pentachloropentadeoxygalactosucrose triacetate; 4,6,1',4',6'-pentachloropentadeoxygalactosorbosucrose triacetate; 4,6, 1',4',6'-pentachloropentadeoxygalactosucrose; 4,6,1',4',6'-pentachloropentadeoxygalactosorbosucrose; 6-0-acetyl-4,1', 6'-tribromo-4,1',6-trideoxygalactosucrose; 1',4':3',6'-dianhydro-4-bromo-4-deoxygalactosucrose; 4-bromo-4-deoxy-D-galactose; 3,6-di-0-benzoyl-1,2-0-isopropylidene-α-D-glucofuranoside; 3,6-di-0-benzoyl-1,2-0-isopropylidene-5-0-methyl-α-D-glucofuranos; 6-chloro-6-deoxy-1,2-0-isopropylidene-5-0-methyl-α-D-glucofuranos; trans-1,2-0-benzylidene-D-glycerol; cis-1,2-0-benzylidene-D-glycerol; cis-1,3-0-benzylidene-2-chloro-2-deoxy-D-glycerol; 4-0-mesyl-1',6'-di-0-tritylsucrose pentaacetate; 6-chloro-6-deoxy-D-mannonolactone; 6-chloro-6-deoxy-D-mannonolactone triacetate; methyl 2-acetamido-2-deoxy-β-D-glucopyranoside; methyl 2-acetamido-2-deoxy-β-D-glucopyranoside triacetate; me 2-acetamido-6-chloro-2,6-dideoxy-β-D-glucopyranoside diacetate; 4-0-mesylsucrose pentaacetate OH-1',6'; me 2-acetamido-6-chloro-2,6-dideoxy-α-D-glucopyranoside diacetate; 4-0-mesylsucrose heptaacetate; 3-0-acetyl-1,2:5,6-di-0-isopropylidene-α-D-glucofuranose; 3-0-acetyl-1,2-0-isopropylidene-α-D-glucofuranose; 3-0-acetyl-6-0-benzoyl-5-bromo-1,2-0-isopropylidene-β-L-idose; 3-0-acetyl-6-0-benzoyl-5-chloro-1,2-0-isopropylidene-α-D-glucose; 6-0-benzoyl-5-chloro-1, 2-0-isopropylidene-α-D-glucofuranose; methyl 2-acetamido-6-chloro-2,6-dideoxy-α-D-glucopyranoside; 2-0-benzoyl-3-chloro-D-glyceraldehyde 2,4-dinitrophenylhydrazone; methyl 4,6-0-benzylidene-2-chloro-2-deoxy-α-

D-mannopyranoside; methyl 3-0-benzoyl-4,6-0-benzylidene-α-D-glucopyranoside; methyl 3-0-benzoyl-4,6-0-benzylidene-2-chloro-α-D-mannopyranoside; 2-chloro-2-deoxy-D-mannitol; 4-(tetra-0-acetyl-β-D-glucopyranosyloxy)benzaldehyde; 6'-chloro-6'-deoxy-2,1': 4,6-di-0-isopropylidenesucrose; methyl 4,6-0-(p-nitrobenzylidene)-α-D-glucopyranoside diacetate; 4,6-0-(p-nitrobenzylidene)-α-D-glucopyranose triacetate; methyl 4,6-0-benzylidene-α-D-glucopyranoside diacetate; me 4,6-0-(m-nitrobenzylidene)-α-D-glucopyranoside diacetate (ax); 6,6'-dibromo-6,6'-dideoxysucrose hexaacetate; methyl 4,6-0-(m-nitrobenzylidene)-α-D-glucopyranoside (eq); 6,6'-diazido-6,6'-dideoxysucrose; me 4,6-0-(m-nitrobenzylidene)-α-D-glucopyranoside diacetate (eq); 6'-bromo-6'deoxysucrose heptaacetate; 6,6'-diamino-6,6'-dideoxysucrose; methyl 6-0-(m-nitrobenzyp-α-D-glucopyranoside; 6'-amino-6'-deoxysucrose; 6-chloro-6-deoxy-D-glucitol pentaacetate; 1,2-0-isopropylidene-6-0-acetyl-α-D-glucofuranose; 3,5-0-benzylidene-1,2-0-isopropylidene-6-O-acetyl-α-D-glucofuranose; methyl 3-0-benzoyl-4,6-0-benzylidene-2-chloro-α-D-glucopyranoside; 6-0-trityl-β-D-glucopyranose tetraacetate; 1,2,3,4-tetra-0-acetyl-β-D-glucopyranose; 6-deoxy-6-fluoro-β-D-glucopyranose tetraacetate; 3,5-benzylidene-1,2-O-isopropylidene-α-D-glucofuranose; 6-deoxy-6-fluoro-D-glucitol pentaacetate; methyl 2,3,4,-tri-0-benzoyl-α-D-glucopyranoside; methyl 6-0-tosyl-α-D-glucopyranoside; methyl 2,3,4-tri-0-acetyl-6-thio-6-S-acetyl-α-D-glucopyranoside; 6-chloro-6-deoxy-D-glucitol (sy); 1,2,3,4-tetra-0-acetyl-6-S-acetyl-6-thio-α-D-glucopyranose; 1,2,3,4-tetra-0-acetyl-6-thio-α-D-glucopyranose dimer; 6-chloro-6-deoxy-D-galactitol; 6-chloro-6-deoxy-D-galactitol pentaacetate; 1,2,5,6-tetra-0-benzoyl-3,4-0-isopropylidene-D-mannitol; 3,4-0-isopropylidene-D-mannitol; 1,2-0-isopropylidene-6-0-tosyl-α-D-glucofuranose (crude); 2,5-di-0-benzoyl-1,6-dichloro-3,4-0-isopropylidene-D-mannitol; 2,5-di-0-benzoyl-1,6-dichloro-D-mannitol; 1,2:3,5-di-0-benzylidene-6-0-tosyl-α-D-glucofuranose; 1,2;3,5-di-0-benzylidene-6-S-acetyl-α-D-glucofuranose; methyl 2,3-anhydro-4,6-benzylidene-α-D-gulopyranoside; 1,3:2,4:5,6-tri-0-ethylidene-D-glucitol; 1,3:2,4-di-0-ethylidene-D-glucitol; 5,6-anhydro-1,3:2,4-di-0-ethylidene-D-glucitol; 1,2:5,6-di-0-isopropylidene-α-D-glucofuranose; 1,2:5,6-di-0-isopropylidene-α-D-allofuranose; 1,2-0-isopropylidene-α-D-allofuranose; 6-chloro-6-deoxy-1,2-0-isopropylidene-α-D-allofuranose; 6-chloro-6-deoxy-D-allose; 2,1':4,6-di-0-isopropylidene sucrose tetraacetate; 1,2:5,6-di-0-isopropylidene-α-D-gulofuranose; 1,2-0-isopropylidene-α-D-glucofuranose; 1,2-0-cyclohexylidene-myo-inositol; 1,2-0-cyclohexylidene-myo-inositol tetraacetate; 6-chloro-6-deoxy-1,2-0-isopropylidene-α-D-glucofuranose; 3,4,5,6-tetra-0-acetyl-myo-inositol; 3,4,5,6-tetra-0-acetyl-myo-inositol hydrate; 3,4,5,6-tetra-0-acetyl-1-chloro-1-deoxy-scyllo-inositol; myo-inositol hexaacetate; 1-chloro-1-deoxy-scyllo-inositol pentaacetate; 1,2-dichloro-1,2-dideoxy-myo-inositol tetraacetate; 1-chloro-1-deoxy-scyllo-inositol; 3-0-benzoyl-1,2-5,6-0-di-isopropylidene-α-D-glucofuranose; methyl 6-chloro-6-deoxy-α-D-mannopyranoside triacetate; 3-0-benzoyl-1,2-0-isopropylidene-5,6-di-0-mesyl-α-D-glucose; methyl 4,6-0-benzylidene-α-D-mannopyranoside; methyl 2,3:4,6-di-0-benzylidene-α-D-mannopyranoside; 6-chloro-6-deoxy-D-mannose; methyl 4,6-0-benzylidene-2-chloro-2-deoxy-α-D-glucopyranoside; 3,6-di-0-benzoyl-1,2-0-isopropylidene-5-0-mesyl-α-D-glucofuranose; 6-0-benzoyl-1-chloro-hexan-2,6-diol (syrup); 3,5,6-tri-0-benzoyl-1,2-0-isopropylidene-β-L-idofuranose; 6,6'-dichloro-6,6'-dideoxy-D-maltose hexaacetate; 3-0-acetyl-6-0-benzoyl-1,2-0-isopropylidene-5-0-mesyl-α-D-glucose; 3-0-acetyl-5,6-di-O-benzoyl-1,2-0-isopropylidene-β-L-idofuranose; 5,6-di-0-benzoyl-1,2-0-isopropylidene-β-L-idofuranose; phenyl 6-chloro-6-deoxy-β-D-glucopyranoside; 6'-chloro-6'-deoxysucrose pentaacetate OH-4,1'; 1,2-0-ethylene-β-D-fructopyranoside; 6'-chloro-6'-deoxysucrose; methyl 6-chloro-6-deoxy-α-D-glucopyranoside triacetate; methyl 2,3-anhydro-4,6-0-benzylidene-α-D-allopyranoside; methyl 4,6-0-benzylidene-2,3-di-O-tosyl-α-D-glucopyranoside; methyl 4,6-0-benzylidene-α-D-altropyranoside; L-1,3,4,5,6-penta-0-benzoyl-2-0-methyl-chiro-inositol; 6-chloro-6-deoxy-α-D-altropyranose tetraacetate; 3,6-anhydro-1,2-0-isopropylidene-β-L-idofuranose 5-chlorosulphate; 3,6-anhydro-1,2-0-isopropylidene-β-L-idofuranose; 2-deoxyglucose; methyl 4,6-0-benzylidene-α-D-galactopyranoside; 4-chloro-4-deoxy-D-galactitol; methyl 4,6-0-benzylidene-2,3-di-0-tosyl-α-D-galactopyranoside; methyl 4,6-0-benzylidene-α-D-idopyranoside; 1,2-dichloro-1,2-dideoxy-myo-inositol; Benzyl 2-acetamido-4-0-(2-acetamido-2-deoxy-3,4,6-tri-0-acetyl-β-D-glucopyranosyl)-2-deoxy-3,6-di-0-acetyl-β-D-glucopyranoside; 4'-chloro-4'deoxysucrose hexaacetate OH-3'; 6-chloro-6-deoxy-1,2-0-isopropylidene-β-D-fructofuranose; 6,6'-dichloro-6,6'-dideoxysucrose pentaacetate OH-1';2-chloroethyl β-D-fructopyranoside; 6-chloro-2,6-dideoxy-α-D-glucopyranose triacetate; 4,6-0-benzylidenesucrose hexaacetate; 5,6-dichloro-5,6-dideoxy-1,2-0-isopropylidene-β-L-talofuranose; 5,6-dichloro-5,6-dideoxy-β-L-talofuranose; Methyl neuraminic acid-5-acetyl-chloride ethyl xanthate; Benzyl 2-acetamido-3,6-di-0-benzyl-2-deoxy-4-0-(3,4,6-tri-0-benzyl-β-D-mannopyranosyl)-α-D-glucopyranoside; Benzyl 4-0-β-D-galactopyranosyl-β-D-glucopyranoside heptaacetate; Benzyl 2-acetamido-4-0-(2-acetamido-2-deoxy-β-D-glucopyranosyl)-2-deoxy-β-D-glucopyranoside; Benzyl 2-acetamido-3,6-di-0-benzyl-2-deoxy-4-0-(3,4,6-tri-0-benzyl-β-D-arabinohexopyran-2-ulosyl)-α-D-glucopyranoside; Ethyl-4,6-0-benzylidene-2-deoxy-2-phthlamido-1-thio-β-D-glucopyranoside; 4,6:2,1'-di-0-isopropylidenesucrose tetraacetate; 3,3',4',6'-tetra-0-acetylsucrose; 3',4'-di-0-acetyl-4,1',6'-trichlorotrideoxygalactosucrose; methyl 4-chloro-4-deoxy-α-D-galactopyranoside; 3,1',4',6'-tetrachloro-3,1',4',6'-tetradeoxyallosorbosucrose; methyl 6-chloro-6-deoxy-α-D-glucopyranoside; galactosucrose; 1',6'-dichloro-1',6'-dideoxysucrose hexaacetate; 6,6'-dichloro-6,6'-dideoxysucrose tetraacetate OH-2,1;2,3-0-isopropylidene-6,1',6'-tri-0-tritylsucrose triacetate; 3-0-acetyl-3',6'-di-0-benzoyl-4,6:2,1'-di-0-isopropylidenesucrose; 4,6:2,1'-di-0-isopropylidenesucrose tetrabenzoate; 4,1',6'-tri-0-mesylsucrose pentaacetate; 4-0-mesylsucrose heptaacetate; 3-acetamido-5,6-di-O-acetyl-1,2-isopropylidene-α-D-allofuranose; methyl 2-acetamido-3-O-acetyl-4,6-di-O-mesyl-α-D-glucopyranoside; methyl 4,6-O-benzylidene-2,3-imino-α-D-mannopyranoside; methyl 4,6-O-benzylidene-2,3-imino-N-p-nitrobenzoyl-α-D-alloside; methyl 3-acetamido-4,6-0-benzylidene-2-O-mesyl-α-D-altropyranosid; methyl 2,3-anhydro-4,6-O-benzylidene-β-D-talopyranoside; methyl N-acetyl-4,6-O-benzylidene-2,3-imino-α-D-mannopyanoside; methyl 4,6-O-benzylidene-α-D-sophoroside tetraacetate OH-3; methyl 2-O-benzoyl-4,6-O-benzylidene-α-D-glucopyranoside; Ethyl-3-0-benzyl-2-deoxy-2-phthlamido-1-thio-β-D-glucopyranoside; methyl 6,6'-dichloro-6,6'-dideoxy-β-D-cellobioside; methyl 2,3-di-O-acetyl-4-O-mesyl-6-thiocyanato-α-D-galactoside; methyl 3-acetamido-3-deoxy-2,4,6-tri-0-mesyl-β-D-glucopyranoside; Me N-acetyl-4,6-O-benzylidene-2,3-dideoxy-2,3-imino-α-D-alloside; Me 4,6-O-benzylidene-2,3-imino-N-(2,4-dinitrophenyl)-α-D-alloside; lactose octaacetate (α/β); Chitobiose oxazoline hexaacetate; hexadecyl 3',4'-0-isopropylidene-β-D-lactoside; methyl 4,6-0-isopropylidene-β-D-glucopyranoside; hexadecyl β-D-lactoside; tetracosyl β-D-lactoside; methyl 3-deoxy-3-fluoro-4,6-0-isopropylidene-β-D-allopyranoside; methyl 3-deoxy-3-fluoro-β-D-allopyranoside; 2-deoxy-2-fluoro-1,3,5-tri-0-(4-chlorobenzoyl)-α-D-ribofuranose; p-Mephenyl 2-azido-346-tri-0-p-chlorobenzyl-1-thio-β-D-galactosid; hexadecyl β-D-lactoside pentaacetate OH-3',4'; methyl 2,3,6-tri-0-benzoyl-α-D-galactopyranoside; Allyl-β-D-chitobioside; trichloroethyl 2-acetamido-2-deoxy-α-D-glucopyranoside triacetate; trichloroethyl 2-acetamido-2-deoxy-β-D-glucopyranoside triacetate; tce 2-acetamido-3-benzoyl-4,6-orthoacetyl-β-D-glucopyranoside; trichloroethyl β-D-chitobioside heptaacetate; (2',2',2'-trichloroethyl) 2-acetamido-2-deoxy-3-0-benzoyl-6-0-acetyl-β-D-glucopyranoside; allyl β-D-chitobioside heptaacetate; 3,4,6-tri-O-benzyl-D-mannose; tetra-O-benzoyl α-D-glucopyranosyl bromide; tetra-O-benzoyl-2-hydroxy-D-glucal; 3,4,6-tri-O-benzoyl-α-D-hexopyranos-2-ulosyl bromide; benzyl α-D-manno(1α3) bioside 6-chloroacetate hexabenzoate; benzyl α-D-manno (1α3)bioside 6-OH hexabenzoate; 2-deoxy-2-phthalimido-β-D-glucosamine tetraacetate; 4-deoxy-4-fluoro-D-galactose; benzyl 2-acetamido-2-deoxy-α-D-glucopyranoside; benzyl 2-acetamido-4,6-O-benzylidene-2-deoxy-α-D-glucoside; benzyl α-D-mannopyranoside; Ethyl-6-0-acetyl-3-0-benzyl-2-deoxy-2-phthlamido-1-thio-β-D-glucopyranoside; benzyl 2-acetamido-6-0-acetyl-3-0-benzoyl-2-deoxy-α-D-glucoside; benzyl 2-acetamido-3-O-benzyl-4,6-O-benzylidene-α-D-glucoside; EtS 2-O-(2-acetamido-β-D-glucopyranosyl)-α-D-mannoside hexaacetate; Benzyl 2,4-di-benzoyl-α-D-mangopentaoside tetradecaacetate; Benzyl 2,4-di-0-benzoyl-3-0-[2-0-(2-acetamido-2-deoxy-3,4,6-tri-0-acetyl-β-D-glucopyranosyl)-3,4, 6-tri-0-acetyl-α-D-mannopyranosyl]-α-D-mannopyranoside; Benzyl 2-acetamido-3-0-(tetra-0-acetyl-β-D-galactopyranosyl)-4,6-0-benzylidene-2-deoxy-α-D-glucopyranoside; Benzyl 2-acetamido-3-0-(tetra-0-acetyl-β-D-galactopyranosyl)-2-deoxy-α-D-glucoside; 1,2:5,6-di-0-isopropylidene-α-D-galactofuranose; 2-O-acetyl-3,4,6-tri-O-benzyl-D-glucopyranose; Benzyl 2-acetamido-4-0-(2-0-acetyl-3,4,6-tri-0-benzyl-(β-D-glucopyranosyl)-3,6-di-O-benzyl-2-deoxy-α-D-glucopyranoside; benzyl 2-acetamido-3,6-di-O-benzyl-2-deoxy-α-D-glucopyranoside; Benzyl 2-acetamido-3,6-di-O-benzyl-4-O-(3,4,6-tri-O-benzyl-β-D-glucopyranosyl)-2-deoxy-α-D-glucopyranoside; 2-O-β-D-glucopyranosyl-D-glucopyranose; Benzyl 4-0(3,4-0-isopropylidene-(β-D-galactopyranosyl)-β-D-glycopyranoside; 2-0-α-D-marmopyranosyl-3,4,6-tri-0-benzyl-D-mannopyranose; 4-methylphenyl 1-thio-β-D-lactoside heptaacetate; 4-methylphenyl 4-0-(2,6-di-0-acetyl-β-D-galactopyranosyl)-2,3,6-tri-0-acetyl-1-thio-β-D-glucopyranoside; 4-methylphenyl 4-0-(3,4-0-isopropylidene-β-D-galactopyranosyl)-1-thio-β-D-glucopyranoside; Ethyl 3-0-benzyl-2-deoxy-2-phthalimido-4-0-β-D-galactopyranosyl-1-thio-β-D-glucoside; Ethyl 2-acetamido-6-0-acetyl-3-0-allyl-2-deoxy-4-0-(tetra-0-acetyl-β-D-galactopyranosyl) 1-thio-β-D-glucopyranoside; Benzyl 2-acetamido-6-0-acetyl-3-0-benzyl-2-deoxy-α-D-glucopyranoside; Benzyl 2,4-di-0-benzoyl-6-0-(tetra-0-benzoyl-α-D-mannopyranosyl)-α-D-mannopyranoside; Benzyl 2-acetamido-6-0-acetyl-2-deoxy-3-0-(tetra-0-acetyl-β-D-galactopyranosyl)-α-D-glucopyranoside; Benzyl 2-acetamido-6-0-acetyl-3-0-(tetra-0-acetyl-β-D-galactopyranosyl)-4-0-(tri-0-benzyl-α-L-fucopyranosyl)-2-deoxy-α-D-glucopyranoside; 1,4,6-tri-0-acetyl-3-0-(tetra-0-acetyl-α-D-galactopyranosyl)-α-D-galactopyranose; 1,4,6-tri-0-acetyl-2-0-(tri-0-benzyl-α-L-fucopyranosyl)-3-0-(tetra-0-acetyl-α-D-galactopyranosyl)-α-D-galactopyranose; Benzyl 4,6-0-benzylidene-α-D-glucopyranoside; Benzyl 2,3-di-0-benzyl-4,6-0-benzylidene-α-D-glucopyranoside; Benzyl 2,3-di-0-benzyl-α-D-glucopyranoside; Benzyl 0-α-D-galactopyranosyl-(1→3)-0-β-D-galactopyranosyl-(1→4)-2,3-di-0-benzyl-α-D-glucopyranoside; Benzyl 2-acetamido-3-0-benzyl-2,6-dideoxy-6-iodo-α-D-glucopyranoside; Benzyl 2-acetamido-3-0-benzyl-2,6-dideoxy-α-D-glucopyranoside; Benzyl 2-acetamido-6-0-acetyl-3-0-benzyl-2-deoxy-α-D-glucopyranoside; Phenyl 2,3,4,6-tetra-0-acetyl-1-thio-α-D-mannopyranoside; 1,3,4,6-tetra-0-acetyl-β-D-mannopyranose; 1,2,3,6-tetra-0-benzoyl-4-0-(2,3-di-0-benzoyl-4,6-0-isopropylidene-β-D-galactopyranosyl)-α& β-D-glucopyranose; 1,2,3,6-tetra-0-benzoyl-4-0-(2,3-di-0-benzoyl-β-D-galactopyranosyl)-β-D-glucopyranose; 1,2,3,6-tetra-0-benzoyl-(2, 3,6-tri-O-benzoyl-β-D-galactopyranosyl)-β-D-glucopyranose; 1,2,3,6-tetra-0-benzoyl-4-0-(2,3-di-O-benzoyl-β-D-galactopyranosyl)-α-D-glucopyranose; 1,2,3,6-tetra-0-benzoyl-(2,3,6-tri-O-benzoyl-β-D-galactopyranosyl)-α-D-glucopyranose; Phenyl 2,3,6-tri-0-benzoyl-1-thio-β-D-galactopyranoside; Phenyl 3,6-di-0-benzoyl-1-thio-β-D-galactopyranoside; Phenyl 1-thio-β-D-galactopyranoside; Benzyl 4-0-(4,6-0-4-methoxybenzylidene-β-D-galactopyranosyl)-β-D-glucopyranoside; Benzyl 4-0-(2,3-di-0-acetyl-4, 6-0-4-methoxybenzylidene-β-D-galactopyranosyl)-2,3,6-tri-0-acetyl-β-D-glucopyranoside; Benzyl 4-0-(2-0-acetyl-3, 4-0-isopropylidene-6-0-4-methoxybenzyl-β-D-galactopyranosyl)-2,3,6-tri-0-acetyl-β-D-glucopyranoside; Benzyl 4-0-(2-0-acetyl-β-D-galactopyranosyl)-2,3,6-tri-0-acetyl-β-D-glucopyranoside; 2,3,6,3',4'-penta-0-acetylsucrose; (4-methyl phenyl)sulphenyl 2-azido-3,4,6-tri-0-(4-chlorobenzyl)-2-deoxy-β-D-galactopyranoside; 4,6-0-(4-methoxybenzylidene)-2-acetamido-2-deoxygalactopyranose; Benzyl 2-acetamido-2-deoxy-3,6-di-0-benzyl-α-D-glucopyranoside; Benzyl 4-0-(4,6-0-benzylidene-β-D-galactopyranosyl)-β-D-glucopyranoside; Benzyl 2,3,6-tri-0-benzyl-4-0-(2,3-di-0-benzyl-4,6-0-benzylidene-β-D-galactopyranosyl)-β-D-glucopyranoside; Benzyl 2,3,6-tri-0-benzyl-4-0-(2,3,6-tri-0-benzyl-β-D-galactopyranosyl)-β-D-glucopyranoside; Ethyl 4,6-0-benzylidene-2-deoxy-2-phthalimido-1-thio-β-D-galactopyranoside; Benzyl 2,3-di-0-benzyl-4,6-0-benzylidene-β-D-galactopyranoside; Benzyl 2,3-di-0-benzyl-4,6-0-benzylidene-β-D-galactopyranoside; 3-0-(2-acetamido-2-deoxy-α-D-galactopyranosyl)-D-galactose; 3-0-(2-acetamido-2-deoxy-α-D-galactopyranosyl)-D-galactose; 1,3,4,6-tetra-0-acetyl-2-deoxy-2-phthalimido-D-glucopyranose; Methyl 3,4,6-tri-0-acetyl-2-deoxy-2-phthalimido-β-D-galactopyranoside; Methyl 4,6-0-benzylidene-2-deoxy-2-phthalimido-3-0-(3,4,6-tri-0-acetate-α-galactopyranoside-1, 2-orthoacetyl)-β-D-galactopyranoside; Methyl 4,6-0-benzylidene-2-deoxy-2-phthalimido-β-D-galactopyranoside; 1,2,4,6-tetra-0-acetyl-3-0-(2,3,4,6-tetra-0-acetyl-α-D-glucopyranosyl)-α-D-glucopyranose; Thiophenyl 2,3,4,6-tetra-0-benzyl-β-D-galactopyranoside; 2,3,4,6-tetra-0-benzyl-D-galactose; Methyl 2-chloro-3-acetamido-2,3-dideoxy-α-D-altropyranoside; Methyl 3-acetamido-2,3-dideoxy-4,6-isoprpylidene-a-D-glucopyranoside; Methyl 2,3-anhydrodideoxy-2,3-acetamido-4,6-0-benzylidene-a-D-allopyranoside; Methyl 2,3-dideoxy-3-acetamido-4,6-di-O-mesyl-a-D-glucopyranoside; Methyl 3-aminohydrochloride-3-deoxy-4,6-benzylidene-a-D-mannoside; 2,1'-isoprpylidene-2',3',4'-tri-O-acetyl sucrose; Methyl a-D-galactoside; Gamma-D-Galactonolactone.

The term "recipe" refers to a mixture of the modulators and their concentrations that will be used to produce said recombinant protein or biosimilar with the target PTMs.

The term "recombinant protein" refers to any protein species, produced in living cells, systems, or organisms resulting from recombinant DNA technology. As used herein, the term "recombinant protein" includes but it is not limited to, proteins, polypeptides, and monoclonal or polyclonal antibodies and their biosimilar versions.

As used herein the term "antibody" encompasses whole antibodies including single chain antibodies, and antigen whole antibodies, and antigen binding fragments thereof. Fab, Fab' and F(ab')2, Fd, single chain Fvs (scFv), single chain antibodies, disulfide-linked Fvs (sdFv) and fragments comprising either VL and VH are all within the present definition of the term "antibody." Antibodies may originate from any animal origin including birds and mammals Preferably, the antibodies are human, murine, rabbit, goat, guinea pig, camel, horse, or chicken.

The term "biosimilar" refers to a recombinant protein, commonly with identical amino acid sequence to a reference commercial product that contains, similar, very similar to or same post-translational modifications as the reference product yielding similar biological activity to that product.

The term "reference product" refers to a currently or previously marketed recombinant protein, also described as the "originator" or "branded product" serving as a comparator in the studies. An "originator" or "branded" product are examples of a reference product.

The term "reference standard" refers to a highly characterized drug substance. The reference standard is prepared during the drug development cycle to serve as a comparator to all subsequent lots being manufactured.

The term "biobetter" refers to a version to an original biological drug with the same protein sequence but post-translational modifications that are outside the target PTM range, which affect the drug's biodistribution, pharmacokinetics and pharmacodynamics.

As used herein, the term "candidate" with reference to biosimilar drug or bio-better drug, refers to the intent that it will be the subject of an application for commercial sale submitted for approval by one or more drug regulatory agencies in one or more different jurisdictions.

Recombinant proteins generally contain post-translational modifications. These modifications include but are not limited to: glycosylation, carboxylation, hydroxylation, O-sulfation, amidation, glycosylation, glycation, alkylation, acylation, acetylation, phosphorylation, biotinylation, formylation, lipidation, iodination, prenylation, oxidation, palmitoylation, pegylation, phosphatidylinositolation, phosphopantetheinylation, sialylation, and selenoylation.

The term "glycosylation" refers to attachment of oligosaccharides to proteins and represents the most commonly found post-translational modification of recombinant proteins. Oligosaccharides consist of monosaccharide units that are connected to each other via glycosidic bonds. Oligosaccharides may also be branched, with each of the sugar units in the saccharide serving as an optional branching point. The oligosaccharide chains are attached to proteins co-translationally or post-translationally, via specific asparagine (N-linked) or serine/threonine (O-linked) residues. For N-linked glycosylation the consensus amino acid sequence of recombinant protein is Asn-X-Ser/Thr. O-sulfation entails the attachment of a sulphate group to tyrosine, serine and threonine residues mediated by sulfotransferases Amidation is characterized by the replacement of the C-terminal carboxyl group of a protein with an amide group. γ-carboxylation and β-hydroxylation modifications are mediated by specific carboxylase and hydroxylase enzymes, with conversion of target glutamate residues to γ-carboxyglutamate (Glu→Gla) and either target conversion of aspartate residues to β-hydroxyaspartate (Asp→Hya) or asparagine residues to β-hydroxyasparagine (Asn→Hyn).

The phrase "post-translational modifications on the recombinant protein are substantially the same as the modifications on the reference protein" can be taken to mean that the levels of post-translational modifications are within the ranges of the post-translation modifications identified in at least five lots of the reference protein.

The method for developing "target PTMs" is described in Examples 1 and 2.

The disclosed method involves developing a media recipe from growing cells to produce a recombinant protein of interest. The media can be any medium that is appropriate for growth of the cells that are used to produce the recombinant protein. The media can include supplements of which concentrations may be known or unknown. Examples of suitable supplements include salts, amino acids, vitamins, lipids, glutamine, glucose and galactose. Growth media for cells can be made custom or purchased commercially from companies like Gibco, Lonza, Millipore, Hyclone, GE and others familiar to those skilled the art of upstream process media development.

Any cell that can be used for the production of the target recombinant protein can be used in the present method. Suitable cells generally will excrete the produced protein into the medium from which the recombinant protein can be isolated. Most commonly used cells are all variants of CHO cells, CAP-T cells, murine myeloma NS0cells, Baby Hamster Kidney (BHK) cells, SP2/0 cells, 293 cells or NSO cells.

The cells can be grown as a batch, as in shake flasks, or in any type and size of bioreactor and/or wave bags for production of the recombinant protein. Manufacturers of growth chambers and apparatuses include but are not limited to those produced by Millipore, General Electric, Eppendorf (New Brunswick), and Sartorius Steadim.

When cultured in a bioreactor, a control mechanism for altering conditions for production of the recombinant protein may be also provided. The mechanism for altering conditions may be in digital data communication with the controller so that an operator may alter production conditions by providing input to the controller. Conditions which may be altered using the controller include, but are not limited to: temperature, pressure, gas flow, agitation, and composition of growth medium components. Examples of growth medium components include, but are not limited to carbohydrates, salts, proteins and lipids and one or more components from the modulator library.

Figure 2:
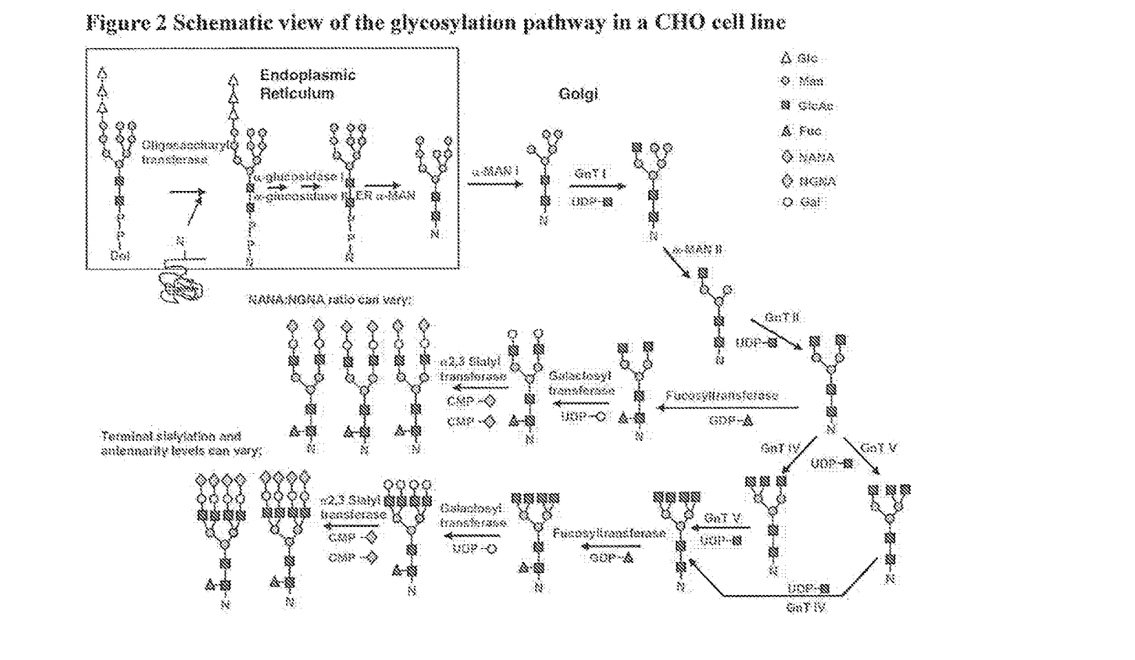
FIG. 2 is a schematic representation of a glycosylation pathway.

Any PTM that can be controlled by the addition or removal of a modulator is amenable to modulation by the present methods. Glycosylation is an example of a PTM that is particularly amendable to the optimization by the present methods as the host proteins involved in the glycosylation pathway are well known (FIG. 2) and can be modulated by a variety of inhibitors (FIG. 2). Other PTMs are described in the definition section.

Any suitable method known to one skilled in the analytical arts can be used for measuring the levels of PTMs. Mass spectrometry (MS) is a powerful method for analyzing and quantifying PTMs. Some of the MS based methods amenable to said analysis may include but is not limited to: intact mass analysis, reduced mass analysis, peptide map analysis, and disulfide linkage analysis. Intact mass analysis by ESI-MS is used for identification and quantitation of PTMs on a recombinant protein including but not limited to glycosylation and C-teiniinal lysine content. To analyze complex molecules such as antibodies, reduced mass analysis and peptide mass analysis should provide detailed infoiniation including the exact amino acid that has been modified. To conduct reduced mass analysis heavy and light chains of the antibody are first reduced, then resolved using reverse phase chromatography or other methods known to one skilled in the art and subsequently analyzed using ESI-MS. To conduct a peptide map analysis, an antibody is first digested with an enzyme that leads to antibody fragmentation. Each peptide is first resolved on appropriate chromatographic media and then analyzed by ESI-MS for amino acid sequence and PTMs such as glycosylation, deamidation, oxidation, disulfide scrambling, and C-terminal lysine content. Enzymes that can be used for recombinant protein digestion include but are not limited to trypsin and Lys-C.

Chromatography by HPLC or UPLC is another powerful method to analyze recombinant proteins. For example, glycan species can be quantitated using a fluorescent 2AB labeling method. In this method, glycans are first removed from the protein by digestion with N-glycanase and then a fluorescent label is added to each glycan. The glycans can then be resolved using HILIC based chromatography and quantitated by measuring relative area under the curve. For oxidation quantitation an HIC based method can be used.

To deteiniine the level of deamidation using chromatography based methods ISOQUANT Isoaspartate Detection Kit can be used. The ISOQUANT Isoaspartate Detection Kit uses the enzyme Protein Isoaspartyl Methyltransferase (PIMT) to specifically detect the presence of isoaspartic acid residues on a recombinant protein. PIMT catalyzes the transfer of a methyl group from S-adenosyl-L-methionine (SAM) to isoaspartic acid at the α-carboxyl position, generating S-adenosyl homocysteine (SAH) in the process. SAH foiniation is then quantitated in the sample by comparing it to the standard provided in the kit.

The methods described herein are useful for optimization of cell growth conditions to produce recombinant proteins with a set of PTMs defined by the reference. The methods described herein are particularly useful during process changes and in biosimilar development. The method involves developing a media recipe to produce a recombinant protein with target PTMs.

In one aspect of the invention, there is provided a method for optimizing PTMs on a recombinant protein during a manufacturing process change via modulation of host protein activity using the following steps:
  a) Measuring different PTMs on the reference standard and other drug batches produced using the original process. Three to five batches are usually recommended by the regulatory agencies however more batches can be examined.
  b) Setting target ranges for the PTMs on recombinant protein produced using a new process. Target ranges are set based on data generated in a).
  c) Selecting a plurality of growth media and one or more modulators which can be selected from a modulator library.
  d) Growing living cells expressing the recombinant protein in the presence of the modulator(s) at different modulator concentrations.
  e) Isolating the product from d) and comparing its PTMs to the target set in b).
  f) Repeating steps c), d) and e) with additional modulators and/or at different modulator concentrations from the ones selected in c) until PTMs set in b) are substantially matched. The modulators can be used alone or in combination with each other. The set of exact modulators required to obtain the target PTMs provides a recipe for the production of said recombinant protein. The PTMs should not be outside the specifications set for said reference standard.

In another aspect of the invention, there is provided a method for optimization of PTMs on a biosimilar via addition of selected set of modulators to influence the activity of the host proteins using the following steps:
  a) Measuring PTMs on the reference product(s). At least three batches of reference product should be analyzed however studying more batches may help to increase the range in target PTMs
  b) Setting target ranges for the PTMs for a biosimilar product
  c) Selecting a plurality of growth media and one or more modulators, which can be selected from a modulator library.
  d) Growing the living cells expressing the biosimilar product in the presence of the modulator(s).
  e) Isolating the product from d) and comparing its PTMs to the target range set in b).
  f) Repeating steps c), d) and e) with additional modulators from the library to obtain a biosimilar product having target PTMs. Modulators can be used alone or in a combination with each other. The exact modulation (type of modulator and its concentration) required to obtain the target PTMs provides a recipe for the production of said biosimilar product.

The modulators are selected to influence the activity of host proteins likely to introduce PTMs on the subject protein. The post-translational modifications may include, but are not limited to any of the following post-translational modifications: glycosylation, carboxylation, deamidation, oxidation, hydroxylation, O-sulfation, amidation, glycylation, glycation, alkylation, acylation, acetylation, phosphorylation, biotinylation, fonnylation, lipidation, iodination, prenylation, oxidation, palmitoylation, phosphatidylinositolation, phosphopantetheinylation, sialylation, and selenoylation, C-Lysine removal.

The described method results in the development of a recipe for media having concentrations of a variety of modulators that are required to produce recombinant proteins matching target PTMs. The recipe is ideally used to produce the recombinant protein after a manufacturing process change or in biosimilar development. The method is particularly useful in the development of biosimilar products having PTMs that are difficult to match and have the advantage that they can be used while keeping cell productivity high because the method decouples the productivity from PTM profile. Examples where the method can be used include trastuzumab biosimilar.

EXAMPLE 1

Setting Target Posttranslational Modifications

This example demonstrates one method for identifying target PTMs for development of a recipe for production of a recombinant protein. In order to identify target PTMs, 3-5 batches of the original reference product should be examined for the type and the amount of specific PTMs. For biosimilar development a reference is defined as reference product. For a process change, a reference is defined as one batch of the reference standard and an additional 4 batches of the product made using the original process. In the example below to set target PTMs for biosimilar development, 5 batches of the reference product were analyzed for PTMs. Out of 14 PTMs, two PTMs (glycosylation—G0 and glycosylation G2 were not observed. Other PTMs were measured and are shown in Table 1 to be present at different levels on different batches. To set the target PTMs, first the exact measurements for each PTM are identified for all five batches 1-5. For example, for Glycosylation—G0 PTM, the 2AB glycan analysis showed variability from 2-6%. To set the target PTM, the range is extended by 1% on the lower limit and 2% on the upper limit yielding a target PTM range of 1%-8%. Using this method target PTMs are set for each PTM.

TABLE 1

Setting Target PTMs

| PTM | Batch 1 | Batch 2 | Batch 3 | Batch 4 | Batch 5 | Target PTM |
|---|---|---|---|---|---|---|
| Glycosylation -G0 | 3.5% | 2% | 5% | 6% | 3% | 1-8% |
| Glycosylation-G1 | 1.5% | 2% | 1.8% | 2.5% | 0.5% | 0-4.5% |
| Glycosylation- G2 | 0% | 0% | 0% | 0% | 0% | 0% |
| Glycosylation -G0F | 45% | 48% | 51% | 44% | 52% | 44-54% |
| Glycosylation- G1F | 20% | 22% | 18% | 16% | 20% | 15-24% |
| Glycosylation- G2F | 4% | 3% | 5% | 4.5% | 6% | 2-8% |
| Glycosylation- Mannose 5 | 1.5% | 1.8% | 1.7% | 1.6% | 1.9% | 0.5-3.9% |
| Glycosylation- Mannose 8 | 0% | 0% | 0% | 0% | 0% | 0% |
| C-terminal lysine content- 2 lysines | 0.5% | 0.8% | 1% | 1.4% | 1.3% | 0-3.3% |
| C-terminal lysine content- 1 lysine | 5% | 4% | 3% | 2% | 4% | 2-7% |
| Deamidation | 3% | 3.5% | 3.2% | 4% | 3.5% | 2-6% |
| Oxidation | 2% | 2.5% | 2.1% | 1.8% | 3% | 0.8-5% |
| Aggregation | 0.5% | 0.4% | 0.5% | 0.4% | 0.3% | 0-2.5% |

EXAMPLE 2

A Recipe for Biosimilar of Herceptin® With a Similar Glycosylation PTMS

Figure 3:
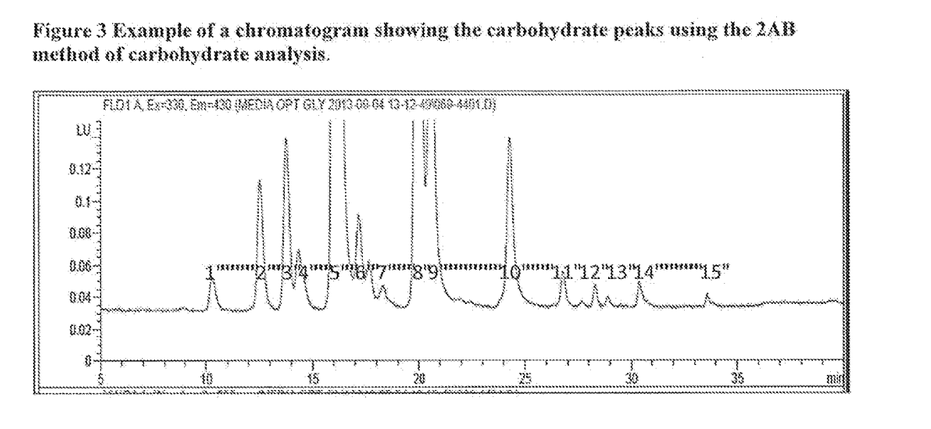
FIG. 3 provides an example of a chromatogram showing the carbohydrate peaks using the 2AB method of carbohydrate analysis.

This example demonstrates one method to obtain a recipe for making a biosimilar of Herceptin® focusing on optimization of the glycosylation pattern. Herceptin® (INN:Trastuzumab) is a humanized monoclonal antibody directed against the external domain of the human HER2. The antibody is an IgG1, consisting of two $\gamma_1$ heavy chains, two κ chains, and a single complex-type biantennary N-linked glycan at Asn300 of the heavy chain. For the purpose of this example Herceptin® (INN: trastuzumab) is a reference product. Five different batches of Herceptin® were analyzed for glycosylation pattern using 2AB glycan labeling method and the results are shown in Table 2. Since the PTM identity for some chromatography peaks remains unknown, not all peaks could be assigned to specific glycan PTMs. Therefore, PTMs have been labeled using peak numbers. An example of a chromatogram showing the glycan peaks representing different PTMs from the 2AB glycan method with labeled peaks is shown in FIG. 3. To set target PTMs, the measurements for each PTM for 5 batches of Herceptin® were first collected. For example for Peak 1 PTM, the range was shown to be 1.7-2.8%. Based on the method shown in Example 1, the target PTM was identified to be 0.7-4.8% (lower limit was extended by 1% and upper limit was extended by 2%).

TABLE 2

Setting Target PTMs For Glycan Species on Herceptin ®

| Glycan Species | H4103 | H0783 | H0790 | H0792 | 911826 | Target PTM range |
|---|---|---|---|---|---|---|
| Peak 1 | 2.3 | 2.8 | 2.2 | 2.0 | 1.7 | 0.7-4.8% |
| Peak 2-G0 | 3.6 | 3.2 | 3.3 | 3.8 | 3.6 | 2.2-5.6% |
| Peak 3 | 1.7 | 1.8 | 1.8 | 1.5 | 3.5 | 0.5-5.5% |
| Peak 4- G0F | 45 | 49 | 47 | 45 | 45 | 44-51% |
| Peak 5 | 1.6 | 2.0 | 1.9 | 2.0 | 0.7 | 0-4% |
| Peak 6-G1 | 1.2 | 1.0 | 1.1 | 1.3 | 1.0 | 0-3.2% |
| Peak 7- G1F/mannose 5 | 0.9 | 0.9 | 1.0 | 0.0 | 1.2 | 0-3.2% |
| Peak 8- (1,6)G1F | 25 | 22 | 24 | 26 | 23 | 21-28% |
| Peak 9 (1,3)G1F | 10.3 | 10.1 | 10.6 | 10.4 | 10.6 | 9.1-12.6% |
| Peak 10 G2F | 5.6 | 4.4 | 4.9 | 5.2 | 6.1 | 3.4-8.1% |
| Peak 11 | 0.9 | 0.8 | 1.0 | 1.2 | 0.6 | 0-3.2% |
| Peak 12 | 0.3 | 0.4 | 0.4 | 0.4 | 0.3 | 0-2.4% |
| Peak 13 | 0.3 | 0.4 | 0.4 | 0.4 | 0.4 | 0-2.4% |
| Peak 14 | 0.7 | 0.8 | 0.8 | 0.9 | 1.0 | 0-3.0% |
| Peak 15 | 0.3 | 0.5 | 0.5 | 0.5 | 0.7 | 0-2.7% |

To obtain a recipe for production of a biosimilar with a similar glycosylation pattern to the original Herceptin®, CHO cells engineered to express the recombinant protein with an amino acid sequence identical to trastuzumab were first grown in the growth media without any inhibitors to establish a Baseline. The glycan species were analyzed using 2AB glycan method. The data generated for the Baseline is shown in Table 3. It was observed that Peak 2 (G0) and Peak 6 (G1), and Peak 7 (mannose-5 and G1') PTMs were lower for the biosimilar than their target PTMs.

G0, G1 and G1' PTMs are non-fucosylated PTMs and are controlled by a host protein called fucosyl transferase and the mannose-5 PTM is controlled by the host protein known as α-mannosidase I. Fucosyl transferase can be inhibited by a variety of fucosyltransferase inhibitors shown in FIG. 2, α-mannosidase I can be inhibited by kifunensine.

The result of optimization is shown in Method 1 in Table 3. Briefly to obtain trastuzumab with PTMs in the target range, cells were placed in growth media and treated with 2F-Peracetyl-Fucose (FTI) on day 7 at different concentrations (20 μM, 10 μM, 5 μM, 1 μM, 0.1 μM) to identify optimal drug concentration. On day 12 cells were harvested and the trastuzumab biosimilar isolated. 2AB glycan analysis of the biosimilar showed that while 20 μM FTI treatment resulted in an increase of G0, G1 and G1' PTMs above that of target PTMs, 10 μM FTI treatment resulted in G0, G1 and G1' levels that matched the target PTM range. When cells were treated with FTI at concentrations lower than 8 μM the PTMs were outside the target range. FTI concentrations used to reach target PTMs are cell specific so it is expected that different concentrations of the FTI or other modulators would be required when a starting cell line is different from the one described in this example.

Different treatment methods such as Method 2 can be used to obtain target PTMs. For example, FTI can be added on a daily basis starting on day 5 (Table 3, Method 2) rather than on Day 7. Treatment of cells expressing trastuzumab biosimilar with FTI at about 1.5-3.5 μM everyday starting on Day 5 produced similar results to the one time treatment on Day 7 described in Method 1. Based on these results, different treatment schedules of FTI (different methods) can be employed to obtain the same effect.

In addition to demonstrating that fucosyltransferase activity can be modulated, this Example also demonstrates modulation of the activity of α-mannosidase I using kifunensine in Method 3. Method 3 demonstrates optimization of the mannose species by addition of kifunensine. Different amounts of kifunensine (KFI) were added on day 7 ranging from about 0.001 ng/ml-100 ng/ml. The ideal concentration was identified as being between about 1-10 ng/ml treated on Day 7. Since mannose-5 PTM is not an important contributor to the biological activity of trastuzumab, this modulator may, but doesn't have to be included, in the recipe depending on the growth media used.

What is claimed is:

1. A method for producing a biosimilar protein by optimizing a growth medium for living cells that produce a recombinant protein having a target set of post-translational modifications, said method comprising:
   a) measuring post-translational modifications on a reference product protein,
   b) setting target post-translational modification ranges for the recombinant protein based on the measured post-translational modifications of the reference product protein,
   c) providing a living host cell that expresses the recombinant protein,
   d) placing said host cells in growth media containing a first set of post-translational modulators having a first set of concentrations,
   e) identifying the post-translational modifications on the recombinant protein and determining the differences between the identified post-translational modifications and the target post-translational modification, ranges based on the reference product protein as determined in step b), and
   if the target post-translational modification of the recombinant protein are not within the target post-translational modification ranges determined in b), then:
   f) developing a second set of post-translational modulators wherein the second set of post-translational modulators may include a different set of modulators from the first set, different concentrations of modulators from the first set, or a combination of different modulators and different concentrations of modulators,
   g) producing the recombinant protein from the cells engineered to express the recombinant protein in a growth media in the presence of the modified second set of post-translational modulators,
   h) isolating the recombinant protein from growth media and comparing its post-translational modifications to the target set of post-translational modifications,
   i) repeating steps e), f), g), and h) until a set of post-translational modulators is identified that can be used to

TABLE 3

Methods for Modulating PTM For A Trastuzumab Biosimilar

| Glycan Species | Baseline-Growth media only | Method 1-10 μM FTI - Day 7 | Method 2-2.5 μM-3.5 μM FTI every day starting at day 5 | Method 3-10 μM FTI and 5 ng/ml KFI on Day 7 | Target PTM range |
|---|---|---|---|---|---|
| Peak 1 | 1.5% | 1.5% | 1.5% | 1.5 | 0.7-4.8% |
| Peak 2-G0 | 1% | 4% | 4% | 4% | 2.2-5.6% |
| Peak 3 | 1.5% | 1.5% | 1.5% | 2% | 0.5-5.5% |
| Peak 4-G0F | 47% | 44% | 44% | 44% | 44-51% |
| Peak 5 | 0.8% | 0.8% | 0.8% | 0.8% | 0-4% |
| Peak 6-G1 | 0.6% | 1.8% | 1.8% | 1.6% | 0-3.2% |
| Peak 7-G1F/mannose 5 | 0.6% | 1.2% | 1.2% | 2% | 0-3.2% |
| Peak 8-(1, 6)G1F | 26% | 26% | 26% | 25.5% | 21-28% |
| Peak 9 (1, 3)G1F | 12% | 11% | 11% | 11% | 9.1-12.6% |
| Peak 10 G2F | 6% | 6.5% | 6.5% | 6% | 3.4-8.1% |
| Peak 11 | 0.2% | 0.2% | 0.2% | 0.2% | 0-3.2% |
| Peak 12 | 0.25% | 0.25% | 0.25% | 0.25% | 0-2.4% |
| Peak 13 | 0.2% | 0.2% | 0.2% | 0.2% | 0-2.4% |
| Peak 14 | 0.2% | 0.2% | 0.2% | 0.2% | 0-3.0% |
| Peak 15 | 0.2% | 0.2% | 0.2% | 0.2% | 0-2.7% | produce a recombinant protein having the target set of post-translational modulations.

2. The method of claim 1, wherein the post-translational modifications on the recombinant protein are the same as the modifications on the reference protein.

3. The method of claim 1, wherein the post-translational modifications on the recombinant protein match the target post-translational modification.

4. A method of making a trastuzumab biosimilar with same or similar post-translational modifications to a reference trastuzumab product said method comprising:
   a) measuring post-translational modifications on different batches of trastuzumab reference product,
   b) setting target post-translational modification ranges for a trastuzumab biosimilar based on the measured post-translational modifications in the reference trastuzumab reference product,
   c) providing a living host cell engineered to express the trastuzumab,
   d) placing said host cell in a cell culture medium in the presence of a first set of post-translational modulators having a first set of concentrations,
   e) identifying the post-translational modifications on the trastuzumab biosimilar protein and determining the differences between the identified post-translational modifications and the target post-translational modification, ranges based on the reference product protein as determined in step b),
   f) developing a modified second set of post-translational modulators wherein the modified second set of post-translational modulators may include a different set of modulators from the first set, different concentrations of modulators from the first set, or a combination of different modulators and different concentrations of modulators,
   g) producing the trastuzumab biosimilar protein from the cells engineered to express trastuzumab in a cell culture medium containing the modified second set of post-translational modulators,
   h) isolating the trastuzumab protein grown in the presence of the modified second set of post-translational modulators from the cell culture and comparing its post-translational modifications to the target set of post-translational modifications,
   i) repeating steps e), f), g), and h) until a set of post-translational modulators is identified that can be used to produce trastuzumab having the target set of post-translational modifications.

5. The method of claim 4, wherein the post-translational modulators identified for producing a trastuzumab having the target set of post-translational modifications comprises fucosyltransferase inhibitor.

6. The method of claim 5, wherein the post-translational modulators identified for producing a trastuzumab having the target set of post-translational modifications consists of a fucosyltransferase inhibitor.

7. The method of claim 4, wherein the post-translational modulators identified for producing a trastuzumab biosimilar having the target set of post-translational modifications comprises a fucosyltransferase and an a-mannosidase I inhibitor.

8. The method of claim 7, wherein the post-translational modulators identified for producing a trastuzumab biosimilar having the target set of post-translational modifications consists of a fucosyltransferase and an a-mannosidase I inhibitor.

9. The method of claim 4, wherein the post-translational modulators identified for producing a trastuzumab biosimilar having the target set of post-translational modifications comprises 2F-Peracetyl-Fucose.

10. The method of claim 9, wherein the post-translational modulators identified for producing a trastuzumab biosimilar having the target set of post-translational modifications consists of 2F-Peracetyl-Fucose.

11. The method of claim 9, wherein the 2F-Peracetyl-Fucose in the growth media is about 0.1 M to about 20 M.

12. The method of claim 4, wherein the post-translational modulators identified for producing a trastuzumab biosimilar having the target set of post-translational modifications comprises a GDP-Fucose derivative.

13. The method of claim 12, wherein the post-translational modulators identified for producing a trastuzumab biosimilar having the target post-translational modifications consists of a GDP-Fucose derivative.

14. The method of claim 4, wherein the post-translational modulators identified for producing a trastuzumab biosimilar having the target post-translational modifications comprises a specific inhibitor of α-mannosidase I.

15. The method of claim 4, wherein the post-translational modulators identified for producing a trastuzumab biosimilar having the target set of post-translational modifications comprises kifunensine.

16. The method of claim 15, wherein the kifunensine in the growth media is about 0.01ng/ml to about 20 ng/ml.

17. The method of claim 4, wherein the mammalian cell is a hybridoma, a CHO cell, CAP-T cells, 293 or an NSO cell.

* * * * *